United States Patent [19]

Shoshan et al.

[11] Patent Number: 5,073,378

[45] Date of Patent: Dec. 17, 1991

[54] PROCESSES FOR THE PREPARATION OF STORAGE STABLE COLLAGEN PRODUCTS

[75] Inventors: Shmuel Shoshan, Motza Elite, Israel; Dov Michaeli, San Francisco, Calif.; Shlomo Magdassi, Jerusalem, Israel

[73] Assignee: Yissum Research Development Company of the Hebrew University of Jerusalem, Jerusalem, Israel

[21] Appl. No.: 286,998

[22] Filed: Dec. 20, 1988

[30] Foreign Application Priority Data

Dec. 22, 1987 [IL] Israel .................................. 84911

[51] Int. Cl.$^5$ ...................... A61K 37/12; A61K 35/32
[52] U.S. Cl. .......................... 424/548; 424/DIG. 13; 514/2; 514/21; 514/755; 514/801
[58] Field of Search ............. 424/95, DIG. 13; 514/2, 514/21, 755, 801

[56] References Cited

U.S. PATENT DOCUMENTS

| | | | |
|---|---|---|---|
| 4,002,739 | 1/1977 | Turner et al. | 514/21 |
| 4,105,798 | 8/1978 | Moore et al. | 514/755 |
| 4,347,243 | 8/1982 | Schneider | 514/801 |
| 4,366,169 | 12/1982 | White | 424/DIG. 13 |
| 4,374,830 | 2/1983 | Schneider | 514/801 |
| 4,760,131 | 7/1988 | Sundsmo | 514/2 |
| 4,789,663 | 12/1988 | Wallace et al. | 514/21 |

FOREIGN PATENT DOCUMENTS

| | | |
|---|---|---|
| 171176 | 2/1986 | European Pat. Off. . |
| 243179 | 10/1987 | European Pat. Off. . |
| 2301568 | 9/1976 | France . |
| 860312 | 6/1986 | PCT Int'l Appl. . |

OTHER PUBLICATIONS

Brown, *Hematology: Principles & Procedures*, 3d ed. Philadelphia, Lea & Febiger, 1980, pp. 68-69.
Ruggerio et al. BA(80)(2): 9815 1985.
Michael W. Mosesson (1977) Thrombos Haemostas. (Stuttg) 38: 742-750 Eva Engvall, et al. (1978) J. Exp. Med. 147: 1584-1595.
Samuel Shoshan (1981) "Wound Healing" in Intl. Rev. Connect. Tissue Res. 9: 1, 4-5.

*Primary Examiner*—Douglas W. Robinson
*Assistant Examiner*—Jean C. Witz
*Attorney, Agent, or Firm*—Felfe & Lynch

[57] ABSTRACT

The invention provides a storage stable lyophilized collagen product comprising acid soluble purified native collagen in combination with platelet derived growth factors and a pharmaceutical composition for enhancing wound healing comprising an aqueous solution of water soluble acid-soluble purified native collagen and platelet derived growth factors.

3 Claims, No Drawings

PROCESSES FOR THE PREPARATION OF STORAGE STABLE COLLAGEN PRODUCTS

The present invention relates to storage stable lyophilized collagen Products, processes for the preparation thereof and pharmaceutical compositions containing the same.

Wound healing has been a phenomenon which has concerned mankind from the inception of his very existence. Physicians, biologists. biochemists and those skilled in other disciplines have endeavored to understand this phenomenon in order to provide better methods and devices to promote such healing. In addition to healing as a chemical and mechanical function, workers have endeavored to understand wound healing in order to provide a finally healed wound with the minimal traces of such trauma. Thus, workers have endeavored to eliminate and reduce scar formation, particularly in the field of burns and excision wounds.

The understanding of wound healing has led to various compositions and methods which have enabled faster healing with minimized scar formation. Collagen has always been recognized as of importance in wound healing. This is because collagen is the main constituent of skin and has always been recognized as a logical ingredient of necessity during the course of wound healing in order to repair tissue. The role of collagen in wound healing is more fully described in "Wound Healing" by Shmuel Shoshan, *International Review of Connective Tissue Research,* Vol. 9(1981). pages 1-26 .

Collagen constitutes the connective tissue and is the major type of fibrous protein in higher vertebrae. Collagen in its natural state exists in a triple chain helix along with a constant periodicity between aligned triple chains. The triple helical configuration of collagen molecules align in fibrils with an axial periodicity of about 640 A.

Although there are several types of collagen, the major type is referred to as "type I" which is the major collagen of skin, bones and tendons. The type I collagen has a chain composition of $[1(I)_2\ 2]$. The $1(I)$ and 2 chains are homologous.

In young animals there is relatively little intermolecular crosslinking which provides for some degree of solubility of the collagen. However, during the aging process there is a relative increase in stable intermolecular crosslinks, thus making most of the collagen insoluble.

Collagen in purified form has been recognized in wound healing. Thus collagen, in substantially pure form and in its fibrous form, has been proposed for many uses including for burn dressings as is disclosed in U.S. Pat. Nos. 3,939,831 and 3,514,518, and similar medical applications as is diclosed in U.S. Pat. Nos. 3,157,524 and 3,628,974. In these medical applications, the collagen in sheet or fibrous form is utilized in external application to the wound or burn to promote healing. The primary advantage of the collagen in this form is that it acts as a hemostat to coagulate blood and also to form a substrate for cell growth.

In another aspect of the utilization of collagen for wound and burn treatment, collagen solutions enriched with various biologically active materials such as antiobiotics, nutrients and the like have been found to enhance wound healing in many fields such as in tooth implants, burns, excision wounds and tendon repair. These developments are reported in "Improvement of Gliding Function of Flexor Tendons by Topically Aplied Enriched Collagen Solution" by Porat et al., *The Journal of Bone and Joint Surgery.* Vol. 68-B. No. 2 (May 1980), pages 208-213; "Enhanced Healing of Tooth-Pulp Wounds in the Dog by Enriched Collagen Solution as a Capping Agent" by Bimstein et al., *Archs Oral Biol.,* Vol. 26 (1981), pages 97-101; "The Effect of Enriched Collagen Solutions on Scar Formation in Third Degree Burns in Animals After Early Surgical Excision of the Slough" by Shoshan et al., *Burns,* Vol. 3, No. 3, pages 153-158; and "Biological Anchoring of Arylic Tooth Implants in the Dog Using Enriched Collagen Solutions" by Jaffe et al., *Archs Oral Biol.,* Vol. 23 (1978), pages 415-419. This reported work with enriched collagen solutions demonstrates that such collagen solutions are effective in promoting wound healing and reduced scar formation. Briefly, the enriched collagen solution is introduced into the wound and collagen fibers form at in vivo temperatures which promote cell growth, act as a coagulant and have the necessary chemotactic properties to attract cells and promote wound healing. The necessary characteristics of such enriched collagen solutions primarily are that they are in solution at ambient temperature, i.e. 15° C. to about 30° C.; however, at in vivo temperatures, i.e. above 35° C., fibers are formed. Thus, in treating wounds with the enriched collagen solution, the solution at below 35° C. is applied to the wound in liquid form so as to penetrate the wound and closely associate with the tissue and upon its heating to the in vivo temperature, forms collagen fibers which function as a wound healing agent. As a practical matter, it has been found that such enriched collagen solutions stay in solution form at temperatures between 0° C. and 34° C., while at temperatures above about 34° C. or 35° C. dissolved collagen molecules aggregate and form fibers, which turns the solution into a semisolid gel.

Although these enriched collagen solutions have been found to be effective in wound healing their practical use has been limited due to problems with storage stability and time required to prepare these enriched collagen solutions. Typically, four to five days are required to prepare the enriched collagen solutions, and thus, such solutions must be prepared well in advance of wound treatment. It was found that such solutions could be prepared and stored at 4° C. and in a deep freeze at −20° C. and retain stability up to 12 weeks. The criteria for stability was that the solutions, when heated to in vivo temperatures, would form the collagen fibers. After 12 weeks storage, there was a noticeable reduction in fiber formation at in vivo temperatures, thus substantially reducing the effectiveness of the enriched collagen solution for wound healing.

After further research and development it has been found that in fact the wound healing process can be divided into five phases:
1. hemostasis;
2. inflammation;
3. collagen synthesis and angiogenesis;
4. epithelization; and
5. scar formation.

Immediately after injury platelets which come in contact with the injury site become activated and aggregate to form a temporary plug to control blood loss. The coagulation cascade is also activated, resulting in a fibrin meshwork which makes a mechanically strong, more permanent plug of the injured vessel.

Within hours of injury phagocytic polymorphonuclear cells (PMNs) move into the wound area to remove cell debris, necrotic tissue and foreign bodies. These cells are then replaced by macrophages, which are also phagocytic cells and which perform the same functions as the PMNs that preceded them.

Once the wound bed has been debrided, fibroblasts move in from the periphery and base of the wound and lay down new connective tissue, primarily collagen, proteoglycans and glycoproteins such as fibronectin. These fibroblast-secreted macromolecules make up the extracellular matrix of the tissue that fills the space created by the wound. In order to sustain the highly cellular and synthetically active tissue, endothelial cells migrate into the tissue to form a rich network of capillaries supplying oxygen and nutrients and removing carbon dioxide and metabolites from the newly forming tissue (also so called "granulation tissue").

When the process of filling the wound space with extracellular matrix is complete two processes take place, epithelial cells migrate from the wound edges to provide the final cellular cover, and at the same time a decline in the fibroblast population and in vascularity occurs, and the tissue assumes the characteristic histology of a scar.

From the above description it is evident that cells move in and out of the wound area and that they do it in a regular predetermined sequence.

In accordance with the present invention it has now been found that the process of wound healing can be enhanced by a composite of collagen and factors obtained from platelets.

More particularly the present invention provides a storage stable lyophilized collagen product comprising acid soluble purified native collagen in combination with platelet derived growth factors.

"Native collagen" as used herein means and refers to collagen which retains its triple helical tertiary structure and is soluble in water in acid media and is capable of forming a fibrous structure at appropriate pH levels, ionic strength and temperatures. The native collagen which is useful in the practice of the invention is purified acid soluble native collagen from a mammalian source, and preferably bovine native collagen. Typically, methods for preparing acid solubilized native collagen are known in the art and several processes for their preparation have been proposed and utilized. Tyically, the native collagen is treated with a base such as sodium hydroxide with sodium sulfate to control the swelling of the fibers. The sodium hydroxide and sodium sulfate eliminate the crosslinkages to provide acid solubilization. Typical acid soluble collagens are disclosed in U.S. Pat. Nos. 4,097,294, 3,637,642 and British Patent No. 1,571,561.

Typically, the starting native collagen solution is at an acidic pH and at a concentration of about 0.15 to 0.6 percent solids by weight in water. The collagen solution should not be below 0.15 percent by weight since sufficient fibers are not formed in vivo to provide ideal wound healing conditions. Above 0.6 percent by weight the collagen solution tends to be supersaturated, thus presenting problems in handling.

Upon forming the substantially pure collagen solution at the acidic pH, the solution is dialyzed to a pH of about 7.4 to about 7.6 which corresponds to the physiological pH in vivo. The dialysis is typically done against a sodium or potassium phosphate buffer and sodium chloride solution buffered with Tris.

In a preferred embodiment of the present invention said product further comprises a perfluorocarbon compound and a non-toxic pharmacologically acceptable emulsifying agent therefor.

The perfluorocarbon compounds are dense liquids of a low surface tension, immiscible with water. Their biomedical importance stems from their ability to dissolve about 40% of oxygen at 37° C. and at an atmospheric pressure (water dissolves only 2.3% oxygen by volume). These compounds are considered as oxygen carriers and releasing agents thus serving as temporary substitutes for blood in severe cases of hemorrhage or ischemia. The chemistry, biology and different uses of the perfluoro chemicals are summarized in Intern,Anesthesiol,Clin.23. Spring 1985. To the best of our knowledge no attempts have been made as yet to use PFC for enhancing tissue repair either alone or in combination with other substances.

Preferably said perfluorocarbon compound is selected from perfluorotripropylamine cis- and trans-perfluorodecalin. perfluoroisopentyltetrahydropyrane, perfluoro-N,N-dimethylcyclohexyl amine, perfluoro 1-methyl decaline and perfluorotributylamine. Especially preferred perfluorocarbon compounds for use in the present invention are selected from cis-perfluorodecalin, trans-perfluorodecalin, perfluoro-1-methyl decalin, perfluorotripropylamine and perfluorotributylamine.

Preferably said emulsifying agent is selected from lecithin Tween 80 and Pluronic F-68. Tween 80 is an ethoxylated sorbitan monooleate and pluronic F-60 is a co-polymer of propylene oxide and ethylene oxide.

The invention also provides a pharmaceutical composition for enhancing wound healing comprising an aqueous solution of water soluble acid-soluble purified native collagen and platelet derived growth factors.

Also provided is a pharmaceutical composition for enhancing wound healing as hereinbefore defined further comprising an emulsion of a perfluorocarbon compound and a non-toxic pharmacologically acceptable emulsifying agent.

For preparing the products of the present invention there is provided a process for preparing a storage stable lyophilized collagen product comprising acid soluble purified native collagen in combination with platelet derived growth factors comprising:

a) combining acid soluble collagen with Platelet rich plasma:
b) incubating said mixture at a temperature of about 34° to 37.5° C. for a period of about 30 to 60 minutes until the formation of a solid gel:
c) cooling said gel at a temperature of about 0° to 4° C. for a period of about 60 to 120 minutes whereupon said gel undergoes dissolution:
d) centrifuging the resulting solution at 15,000–35,000 RPM for 15-25 min. to remove insoluble collagen, platelet membranes and cell debris whereby there is obtained a supernatant containing soluble collagen and platelet release products, and
e) lyophilizing said solution to form a stable lyophilized product.

Alternatively a process for preparing a storage stable lyophilized collagen product as herein before defined comprises the additional step of combining the solution of steped width an emulsion of a perfluorocarbon compound and a non-toxic pharmacoliogically acceptable emulsifying agent and then lyophilizing the resulting emulsion solution to form a stable lyophilized product.

For preparing pharmaceutical compositions ready for use there is provided a process comprising:

a) combining acid soluble collagen with platelet rich plasma;

b) incubating said mixture at a temperature of about 34° to 37.5° C. for a period of about 30 to 60 minutes until the formation of a solid gel;

c) cooling said gel at a temperature of about 0° to 4° C. for a period of about 60 to 120 minutes, whereupon said gel undergoes dissolution;

d) centrifuging the resulting solution at 15,000-35,000 RPM for 15-25 min. to remove insoluble collagen, platelet membranes and cell debris whereby there is obtained a supernatant containing soluble collagen and platelet release products, e) combining said solution with a perfluorocarbon compound and a Pharmacologically acceptable emulsifying agent; and f) introducing molecular oxygen into said solution to combine with said perfluorocarbon compound, whereby said perfluorocarbon compound serves as an oxygen carrying and releasing agent in said composition.

As already reported by Elaine W. Raines et al, in Methods of Enzymology Vol. 109 (1985) pp. 749-773, Platelet-derived growth factor (PDGF), a 30,000 molecular weight glycoprotein released from the platelet during coagulation, has been shown to be one of the principal macromolecules in whole blood serum capable of stimulating DNA synthesis and cell growth in connective tissue cells in vitro. Although the same molecule has been purified and characterized as PDGF by all four laboratories working on the platelet mitogen, PDGF acounts for approximately 50% of the mitogenic activity found in platelets. The other 50% is probably due to more than one growth factor, already known, e.g., TGF-b and probably more to be discovered. As a potent mitogen for fibroblasts and smooth muscle cells that is released focally at sites of injury, PDGF play a physiologic role in wound healing and tissue repair and a pathologic role in the formation of lesions of atherosclerosis.

Thus the preparation and benefits of PDGF are already known and described in the literature, e.g. PCT Appln. Pub. no. WO-86/03122, however, its combination for simultaneous application with collagen not as a carrier but as a sole platelet activating agent has heretofore not been suggested. It is important to note that, although each component of the composite can by itself enhance somewhat the healing process, the combination produces far superior results, as described hereinafter.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Collagen Source and Purification

Collagen type I from any mammalian source can be used. In the following Examples two sources of collagen were used:

1. Bovine skin collagen digested with pepsin. This is an article of commerce (Zyderm, manufactured by Collagen Corp.) and is composed of acid-soluble bovine skin collagen.

2. Bovine skin collagen, acid-extracted and purified by NaCl precipitation, as described in *Methods in Enzymology*, vol. 82, p.3-217, Academic Press, 19182.

Platelets

Three sources of platelets were used: human blood, rabbit blood and bovine blood. Platelet-rich plasma was obtained by centrifugation of blood at 800 g for 10 minutes.

Platelet Release

Platelet release was accomplished using a variety of techniques:

1. (according to the prior art) Thrombin. 1-5 units, was sufficient to cause the release reaction in about 50 ml of PRP. After 30-60 minutes of incubation with thrombin the PRP was centrifuged at 20,000 g to remove platelet membranes and cell debris. However, thrombin remained in the supernatant.

2. (according to the present invention) Collagen at a concentration of 1-3 mg/ml was mixed with PRP, with concentrations of platelets ranging from the concentration present in normal serum to a concentration approximately 66-fold that. The mixture was incubated at 37° C. for 30 minutes. This resulted in the formation of a solid gel. At the end of the incubation period the gel was cooled to 4° C. for 30-90 minutes. This resulted in its dissolution. The collagen solution was then centrifuged at 20,000 g to remove insoluble collagen, platelet membranes and cell debris. The supernatant contained soluble collagen and the products of the platelet release reaction.

The supernatant can either be used immediately, or stored as such in the cold above freezing temperature, e.g., between 0°-+5° C. up to one week, or freeze-dried for later use for up to 12 months,. stored in a deep freezer at −20° C. Thus aliquots of 5 ml of the supernatant are distributed in 10 ml vials frozen at −70° C. and dried under vacuum (lyophilized). All procedures are carried out under sterile conditions. When needed, the dried material contained in the vial is reconstituted with 5 ml sterile cold distilled water and applied onto the wound.

3. (according to the prior art) Other substances that cause the platelet reaction in a specific way are epinephrine, ADP and arachidonic acid. Nonspecific treatment of platelets can also be utilized to effect the release of their contents, for instance, repeated cycles of freezing and thawing, use of detergents, disruption of the platelet membrane by use of homogenizers, etc.

As described hereinbefore the supernatant solution containing soluble collagen and platelet release products including PDGF is preferably further modified by the addition of about 0.15-0.30 ml of a perfluorocarbon emulsion consisting of 20-60% of perfluorodecaline. perfluorotributylamine or a combination of both or other perfluorocarbons in lecithin or other emulsifiers and saturating it with molecular oxygen by streaming-in for 1-5 minutes using a syringe needle.

EXAMPLE 1

The combination of collagen and platelet release products containing PDGF was tested for wound healing activity by impregnating it into polyvinyl alcohol (Ivalon ®) sponges which were implanted subcutaneously in rats. After a period of time (seven days) the PVA sponge was retrieved from the animal, histologically stained and microscopically examined for invasion of cells and deposition of extracellular matrix in the sponge spaces. The extent of fibroblast and endothelial cell infiltration is a measure of the ability of the composition to promote healing by attraction of repair cells into the area.

In one group of experiments using the in-vivo test technique outlined above PVA sponges alone, PVA sponges impregnated with collagen (2 mg/ml) alone in saline, or collagen (2 mg/ml) in combination with various concentrations of platelet release products were implanted in test animals. After seven days the implants were removed and examined microscopically to determine the degree of fibroplasia (fibroblast infiltration), angiogenesis (endothelial cell infiltration) and inflammation. The slides were read in a blind fashion and were scored on a scale of 1-4, in which 1 denotes little or no infiltration (by fibroblasts, blood vessels or inflammatory cells, as the case may be) and 4 denotes an extreme degree. Table 1 below sets forth the results.

| Preparation | fibro-plasia | angio-genesis | inflammation |
|---|---|---|---|
| sponge only | 1 | 1 | 2 |
| sponge + collagen | 2 | 2 | 1 |
| sponge + collagen + platelets (500,000/mm$^3$) | 2 | 2 | 1 |
| sponge + collagen + platelets (3.3 × 10$^6$/mm$^3$) | 3 | 3 | 1 |
| Sponge + collagen + platelets 33 × 10$^6$/mm$^3$ | 4 | 4 | 3 |

From the above it will be noted that compositions including platelets between $3.3 \times 10^6/mm^3$ and $33 \times 10^6/mm^3$ gave superior results in terms of fibroplasia and angiogenesis.

EXAMPLE 2

The capacity of the platelet products to attract fibroblasts was independently tested in the Boyden chamber (Boyden, J. Expl.Med. 115-453 et seq. 1962). Fibroblasts were placed in the solution in one half of the Boyden chamber, while the platelet release products were dissolved at low concentrations in the second half of the chamber. The two halves of the chamber are separated by a semipermeable membrane. Migration of the fibroblasts to and through the semipermeable membrane is subsequently noted by microscopic examination. In table 2, below, there is presented some data obtained from a series of Boyden chamber tests on a number of concentrations of platelet release products.

| Material tested | fold increase in chemotaxis over control |
|---|---|
| control (saline) | 1 |
| platelet release 1 uL | 2.5 |
| platelet release 10 uL | 14 |
| platelet release 20 uL | 17 |

EXAMPLE 3

In another test the capacity of platelet release products to induce angiogenesis was examined by the rabbit cornea implant assay, described in Gimbrone Jr M. A., Cotran R. S., Leapman S. B., Folkman J. J Natl Cancer Inst. 52: 413-427, 1974. The test solution was mixed with an equal volume of Hydron (Hydron Laboratories, New Brunswick, N.J.), dropped in 20 uL aliquots onto a polyethylene sheet, then dried under vacuum. The resulting pellets of polymerized Hydron containing platelet release products were implanted in corneas 2 mm proximal to the superior limbus. The eyes were evaluated every day for 14 days after implantation. Growth of capillaries from the limbus toward or into the implant was considered positive for angiogenesis. Angiogenic response was scored blindly on a 0-4 relative scale. A normal or negative eye was scored as 0, whereas a maximal response was scored as 4. Results of this test are summarized in the following table 3.

| test material | angiogenic response |
|---|---|
| saline | 0 |
| platelet release 1 uL | 1 |
| platelet release 3 uL | 2 |
| platelet release 10 uL | 4 |

It is evident from the above table that platelet release products can effect a powerful angiogenic response.

The collagen in this preparation serves two major functions. It forms fibers that provide tracks on which cells move preferentially, and thus facilitates and enhances the cellular response to platelet release products. In addition, it constitutes a matrix that retards the diffusion of the platelet release products away from the wound, thus ensuring their prolonged activity.

EXAMPLE 4

To test the effect of collagen-platelet preparation on the closure of an actual skin wound in-vivo, full-thickness skin defects on the back of guinea pigs were treated with either of the following:

a. collagen only (the same as in PVA experiments)
b. platelets only ($5 \times 10^6$/ml)
c. collagen + platelets (the same as in PVA experiments)
d. untreated The effect of the different treatments on healing was followed daily by measuring the wound area and histologically after ten days by measuring the advance of epithelialization using a micro grid put into the eyepiece of a microscope.

Finally, to test the effect of the complete collagen composite of the healing process, another series of guinea pigs were wounded and treated with the collagen-platelet mixture to which 0.25 ml/ml of a perfluorocarbon compound designated FC-45 (purchased from Sigma) was added after being emulsified with lecithin in an oil/water emulsion in which the concentration of the dispersed phase was 20-60 percent.

In the experiments with PFC, the complete collagen composite was Prepared by adding 0.25 ml of the emulsion to each ml of the collagen platelet mixture, usually by adding one ml of PFC to 4 ml of the collagen-platelet mixture, all in a sterile 10 ml air-tight vial from which the air had been replaced by oxygen streamed in with a syringe needle. The vial was well shaken before the contents had been drawn from it for application onto the open wounds. Some wounds were treated with PFC only. The results are summarized on Table 4.

TABLE 4

| Mode of treatment | percent of wound area closed after day | | | | | | | | | | relative epithelial advance at day 10 |
|---|---|---|---|---|---|---|---|---|---|---|---|
| | 1 | 2 | 3 | 4 | 5 | 6 | 7 | 8 | 9 | 10 | |
| Untreated | 7.2 | 15.6 | 20.2 | 25.2 | 34.0 | 41.2 | 56.3 | 59.3 | 64.5 | 72.4 | 2.4 |
| Collagen only | 12.8 | 21.4 | 24.2 | 31.7 | 44.6 | 53.8 | 63.2 | 70.5 | 74.8 | 80.0 | 3.8 |
| Platelets only | 8.5 | 12.6 | 21.0 | 26.4 | 32.6 | 43.7 | 51.8 | 57.3 | 66.1 | 69.9 | 2.6 |
| PFC only | 11.8 | 19.9 | 21.4 | 29.8 | 31.7 | 47.8 | 58.1 | 64.2 | 70.5 | 73.4 | 2.0 |
| Collagen + Platelets | 17.4 | 24.3 | 36.7 | 47.5 | 58.0 | 67.3 | 79.5 | 84.0 | 94.8 | 100 | 8.2 (complete) |
| Collagen + Platelets + PFC | 24.0 | 30.6 | 42.5 | 59.4 | 78.2 | 86.6 | 90.5 | 100 | 100 | 100 | 8.9 (complete*) |

*A conspicuous feature of the epithelium in this group was its almost normal thickness and the presence of well formed rete pegs.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. The process for preparing a storage stable lyophilized collagen product comprising acid soluble purified native collagen and platelet derived growth factors comprising:
    a) combining acid soluble collagen with platelet rich plasma;
    b) incubation said mixture at a temperature of about 34° to 37.5° C. for a period of about 30 to 60 minutes until the formation of a solid gel;
    c) cooling said gel at a temperature of about 0° to 4° C. for a period of about 60 to 120 minutes, whereupon said gel undergoes dissolution;
    d) centrifuging the resulting solution at 15,000-35,000 RPM for 15-25 min. to remove insoluble collagen, platelet membranes and cell debris whereby there is obtained a supernatant containing soluble collagen and Platelet release products, and
    e) lyophilizing said solution to form a stable lyophilized product.

2. A process for preparing a storage stable lyophilized collagen product according to claim 1 comprising the additional step of combining the solution of step d with an emulsion of a perfluorocarbon compound and a non-toxic pharmacologically acceptable emulsifying agent and then lyophilizing the resulting emulsion solution to form a stable lyphilized product.

3. A process for preparing a pharmaceutical composition for enhancing wound healing comprising:
    a) combining acid soluble collagen with platelet rich plasma;
    b) incubating said mixture at a temperature of about 34° to 37.5° C. for a period of about 30 to 60 minutes until the formation of a solid gel;
    c) cooling said gel at a temperature of about 0° to 4° C. for a period of about 60 to 120 minutes, whereupon said gel undergoes dissolution;
    d) centrifuging the resulting solution at 15,000-35,000 RPM for 15-25 min. to remove insoluble collagen, platelet membranes and cell debris whereby there is obtained a supernatant containing soluble collagen and platelet release products including platelet derived growth factors:
    e) combining said solution with a perfluorocarbon compound and a pharmacologically acceptable emulsifying agent; and
    f) introducing molecular oxygen into said solution to combine with said perfluorocarbon compound, whereby said perfluorocarbon compound serves as an oxygen carrying and releasing agent in said composition.

* * * * *

UNITED STATES PATENT AND TRADEMARK OFFICE
CERTIFICATE OF CORRECTION

PATENT NO. : 5,073,378                                    Page 1 of 2

DATED     : December 17, 1991

INVENTOR(S) : Shoshan et al.

It is certified that error appears in the above-identified patent and that said Letters Patent is hereby corrected as shown below:

| | |
|---|---|
| Col. 1, line 6: | change "Products" to -- products --. |
| Col. 3, line 18: | change "(also so called" to -- (also called --. |
| Col. 3, line 47: | change "Tyically" to -- Typically --. |
| Col. 3, line 53: | change "4,097,294" to -- 4,097,234 --. |
| Col. 4, line 65: | change "steped" to -- step d --. |
| Col. 4, line 65: | change "width" to -- with --. |
| Col. 5, line 17: | change "Pharmacologically" to -- pharmacologically --. |
| Col. 5, line 40: | change "focally" to -- locally --. |
| Col. 8, line 68: | change "was Prepared" to -- was prepared --. |

UNITED STATES PATENT AND TRADEMARK OFFICE
CERTIFICATE OF CORRECTION

PATENT NO. : 5,073,378

DATED : December 17, 1991

INVENTOR(S) : Shoshan, et al

It is certified that error appears in the above-identified patent and that said Letters Patent is hereby corrected as shown below:

Col. 5, line 40: change "play" to --plays--.

Signed and Sealed this

Tenth Day of August, 1993

Attest:

MICHAEL K. KIRK

Attesting Officer

Acting Commissioner of Patents and Trademarks